United States Patent [19]
Lim et al.

[11] Patent Number: 5,520,707
[45] Date of Patent: May 28, 1996

[54] METHODS FOR DYEING HAIR WITH ANTHRAQUINONE HAIR DYES HAVING A QUATERNARY AMMONIUM SIDE CHAIN

[75] Inventors: Mu-Ill Lim, Trumbull; Linas Stasaitis, Fairfield; Yuo-Guo Pan, Stamford, all of Conn.

[73] Assignee: Clairol, Inc., New York, N.Y.

[21] Appl. No.: 511,669

[22] Filed: Aug. 7, 1995

[51] Int. Cl.⁶ ............................................. A61K 7/13
[52] U.S. Cl. .................. 8/426; 8/405; 8/606; 8/657; 8/675
[58] Field of Search .................. 8/405, 407, 426, 8/606, 675, 657; 552/255

[56] References Cited

U.S. PATENT DOCUMENTS

| | | | |
|---|---|---|---|
| 3,442,895 | 5/1969 | Bugant et al. | 8/426 |
| 3,823,169 | 7/1974 | Staub | 8/675 |
| 4,009,189 | 2/1977 | Baserga | 8/675 |
| 4,123,222 | 10/1978 | Loew | 552/255 |
| 4,168,144 | 9/1979 | Curry et al. | 8/426 |
| 4,296,044 | 10/1981 | Duchardt et al. | 552/255 |
| 4,393,007 | 7/1983 | Priester et al. | 552/255 |
| 4,655,970 | 4/1987 | Priester et al. | 552/255 |
| 4,886,517 | 12/1989 | Bugaut et al. | 8/405 |

FOREIGN PATENT DOCUMENTS

| | | |
|---|---|---|
| 2712290 | 9/1977 | Germany. |
| 979869 | 1/1965 | United Kingdom. |
| 1475081 | 6/1977 | United Kingdom. |

Primary Examiner—Paul Lieberman
Assistant Examiner—Caroline L. Dusheck
Attorney, Agent, or Firm—Morton S. Simon

[57] ABSTRACT

Anthraquinone compounds of formula I

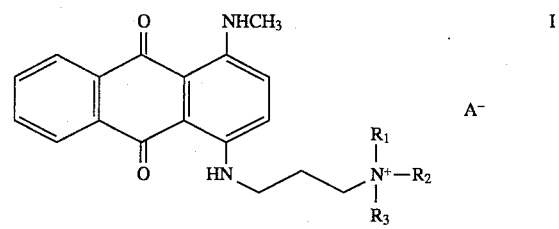

wherein $R_1$ and $R_2$ are methyl and $R_3$ is propyl, or $R_1$ and $R_2$ are ethyl and $R_3$ is methyl and $A^-$ is a cosmetically acceptable anion, are useful for the dyeing of hair. Compounds of formula I may advantageously be employed with direct dyes. Compositions and a method of use employing same are disclosed.

5 Claims, No Drawings

METHODS FOR DYEING HAIR WITH ANTHRAQUINONE HAIR DYES HAVING A QUATERNARY AMMONIUM SIDE CHAIN

DISCUSSION OF THE PRIOR ART

Anthraquinone compounds having a quaternary ammonium side chain and their use as hair dyes are known in the art. The prior art appreciates that there would be problems in formulating a hair dye product with dyes that have different rates of dye uptake and that positively charged dyes (i.e. basic dyes) have qualitatively different rates of dye uptakes than typical neutral semipermanent dyes (i.e. direct dyes). However, it is totally unappreciated that minor variations in the side chain containing the quaternary ammonium group can vary the dye uptake rate (as indicated by the color change on hair) sufficiently so that dyes with certain groups will dye at rates similar to an uncharged semipermanent dye. In point of fact in the hair conditioning art, wherein cationic materials are employed, there is a teaching that would lead one skilled in the art to conclude that modifications in the side chain of the cationic material will have no effect on the rate of adsorption onto the hair.

U.S. Pat. No. 4,964,874 describes some of the problems associated with formulating a product with both basic dyes and neutral dyes. Patentees teach that when using certain basic dyes, color uptake by the hair is rapid in that only a short treatment time of a few minutes is needed to achieve a moderate darkening of the hair. Unacceptable hand staining can, however, occur when the concentration of the basic dye is sufficiently high to achieve adequate dyeing.

Patentees also teach that when using certain neutral dyes, uniform dye coverage can be obtained, but the color uptake by the hair is slower than with basic dyes, in that a longer treatment time is needed to achieve a moderate darkening of the hair. Patentees state that little or no hand staining is experienced with neutral dyes at concentrations sufficient to give adequate dyeing which is usually higher than that of the basic dye.

Differences in rates of dye uptake can lead to another problem. Many hairdye formulations are made by a combination of yellow, red and blue dyes, in different amounts and ratios. In order to incorporate a new dye into an existing product, its rate of dyeing must be comparable to the other dyes in that particular formulation. If a hair dye product containing individual dyes which are picked up by hair at significantly different rates, is applied to the hair, the shade (i.e. the color as opposed to the intensity) will change through several stages with the passing of time. For example, if the product contains blue, yellow and red dyes with the blue dye dyeing the fastest, the yellow dye dyeing at an intermediate rate and the red dye dyeing the slowest, initially, the hair will be bluish. After a certain period of time, the hair will turn greenish (blue plus yellow) and, finally, when the red dye imparts its color, the hair might exhibit a brown coloration. Although this is an exaggerated case even smaller variations would be totally unacceptable (i.e. from a bluish brown to a greenish brown). Clearly, from a consumer's point of view, a product which dyes hair in such a manner is undesirable because the consumer would never be sure of obtaining the hair color that he or she wants or even the same color from the same formulation. Obtaining the exact color is a crucial factor for a hairdye product and this is why most products offer between 25 and 50 different shades.

In a recent paper, C. R. Robbins et al (J. Soc. Cosmet. Chem. 45(2), 85–94, (1994)), report the results of a study of the adsorption onto hair of the following cationic surfactants.

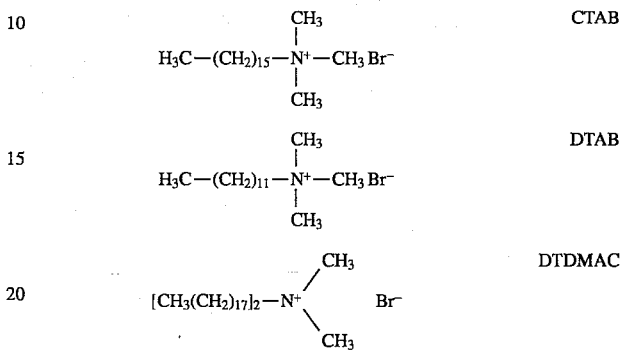

They report that at a pH higher than hair's isoelectric point, all of these hair conditioners had the same adsorption in 10 minutes. This teaching demonstrates that modification of the alkyl groups of the quaternary ammonium conditioners has no effect on the rate of their adsorption of such conditioners onto hair. As a consequence of this teaching, one skilled in the art would expect that modification of the alkyl groups on basic anthraquinone dyes would, like the conditioning agents of this reference, have little or no effect on dye uptake.

British patent 909,700 discloses a method of dyeing human hair. A wide range of dyes having cationic charges is disclosed. Among such dyes are the compounds of Examples 17 and 2. Their respective structures are as follows:

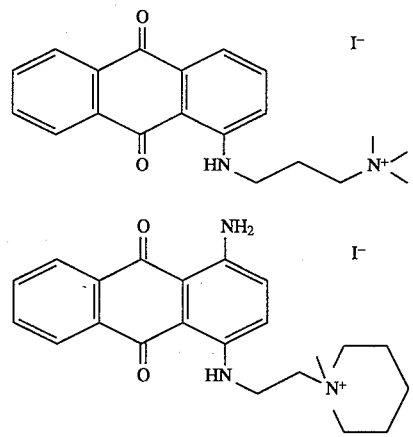

Hair was only dyed with mixtures of compounds containing quaternary ammonium groups. These dyes were never tested with standard nitro dyes.

U.S. Pat. No. 3,817,698 discloses a dye formed by a covalent bond between two dye compounds. In Example 10, patentees disclose the compound:

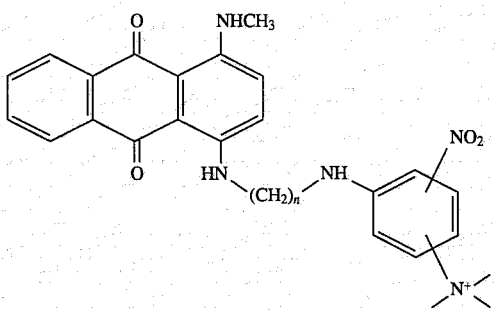

Patentee state, at column 7, lines 11–24, that "It is known that the technique for dyeing different natural and synthetic fibers is based on the use of a greater or smaller number of individual dyes used collectively. The action of such mixtures during the dyeing often poses serious problems, particularly as concerns the harmonization of the different affinities of dyes used simultaneously and harmonization of the speed with which they act on the fibers and of their fastness to washing. Consequently, users frequently discover significant difficulties as much from the point of view of the formulation of these mixtures as from the point of view of their application. Use of dyes according to the invention partly solves the problem since a single dye has the tinctorial properties of the two dyes from which it was formed."

British patent 1,053,535 discloses a dyestuff of the formula:

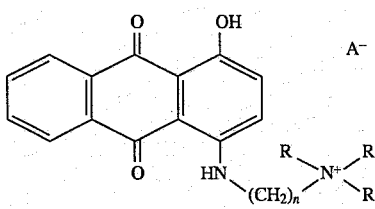

in which n is an integer from 2 to 6 and R, R' and R" are the same or different and each represents an alkyl of 1 to 3 carbon atoms, such as, for example, methyl or ethyl. Alternatively, R, and R', together with the adjacent nitrogen atom, can represent a saturated monocyclic heterocyclic radical, especially a morpholino or piperidino radical. All of the examples describe hair dyeing with compositions containing only the dye described above and the problem of different rates of uptake is not mentioned.

British patent 1,053,536 is closely related to British patent 1,053,535, except that the dyestuffs of the '536 patent contain no hydroxyl substituent on the ring and the substituted amino alkyl amino group is at the 2' rather than the 1' position on the ring. (2-Anthraquinonylaminoethyl)-diethylmethylammonium methylsulfate and (2-anthraquinonylaminopropyl)-diethylmethylammonium methylsulfate are examples of the dyestuffs disclosed. Like British Patent 1,053,535, British Patent 1,053,536 does not refer to the problem of different rates of dye uptake.

U.S. Pat. No. 3,531,502 discloses 1-hydroxy-2,4-bis-(p-dimethylaminophenyl)aminoanthraquinone and a quaternary salt having the formula

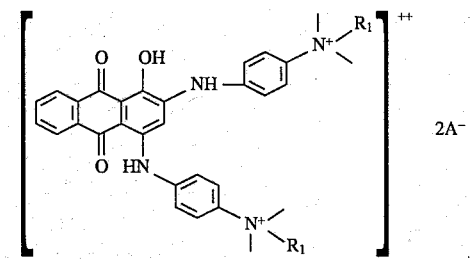

in which $R_1$ is $C_{1-4}$ lower alkyl and $A^-$ is an anion. Such compounds are disclosed to have utility as hair dyes.

U.S. Pat. No. 3,692,461 is related to U.S. Pat. No. 3,531,502 and directed to hair dye composition comprising a solvent and the quaternary ammonium salt of U.S. Pat. No. 3,531,502. In both the '461 patent and the '502 patent, there is only one example (#7) in which these dyes are mixed with an uncharged dye and since this solution was dyed for one length of time, the problem of different rates of dye uptake would not be apparent.

British patent 1,205,365 claims anthraquinone derivatives of the formula

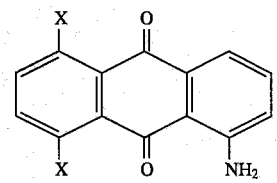

in which one X is hydrogen and the other X is $-NH(CH_2)_nY$ wherein n is 2 to 6 and Y is $-NR^1R^2$, where $R^1$ and $R^2$ are alkyl groups having from 1 to 4 carbon atoms or, together with the nitrogen atom to which they are attached, form a saturated heterocyclic ring which may contain an additional heteroatom, or Y is an aromatic heterocyclic ring attached to the alkylene chain $-(CH_2)_n-$ though a carbon atom. Also, encompassed are the acid addition and quaternary ammonium salts of such compounds. The compounds are disclosed to be useful for dyeing keratinaceous fibers. Included among such anthraquinone derivatives are 1-amino- 5-(γ-piperidinopropylamino) anthraquinone, 1-amino-5-γ-trimethylaminopropylamino) anthraquinone methylsulfate and 1-amino- 8-(γ-trimethylaminopropylamino)anthraquinone methylsulfate. All of the examples describe hair dyeing with only one dye at a time. The dyes which were employed are the subject of the patent.

Ger. Offen. 2,026,096 discloses anthraquinone hair dyes having the structure

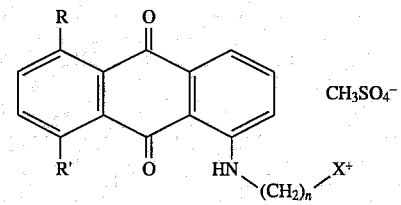

wherein R or $R^1$ is amino and $X^+$ is $N^+(CH_3)_3$, 1-methylpiperidinio or 1-methylpyridinium-2-yl and n is 2 or 3. The compounds dye human hair dark red to reddish violet shades. The dyes of this patent were tested individually and there is no appreciation that that the rate of dye uptake for such dyes differ from typical semipermanent dyes.

U.S. Pat. No. 4,226,784 discloses 2- and 5- aminoalkylamino anthraquinone dyes useful as basic dyes in coloring hair. The compounds conform to the formula A—NR—(CH$_2$)$_n$—NHR', wherein R and R' are hydrogen, n is 2 to 6 and A is anthraquinonyl (in which case the NR—(CH$_2$)$_n$—NHR' chain is in position 2 of the anthraquinonyl) or A is an anthraquinonyl of the formula

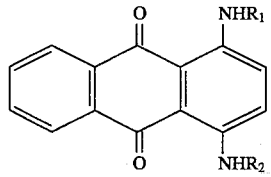

wherein R$_1$ and R$_2$ are selected from the group consisting of hydrogen and lower alkyl and NR—(CH$_2$)$_n$—NHR' occupies position 5 of the anthraquinonyl. 2-β-Aminoethylamino anthraquinone and 1,4-diamino-5-γ-aminopropylamino anthraquinone are specifically disclosed. Different rates of dye uptake are not mentioned in this patent but of the ten hair dyeing examples cited, five contain only one dye, four are mixed with other dyes that have the same side chain and in only one case (Example #10) are these dyes mixed with a typical semipermanent dye (1-amino-2-nitro-4-methylamino benzene). Therefore, the problem of different rates of dye uptake would not have been apparent.

U.S. Pat. No. 3,806,525 discloses a basic anthraquinone dye for keratinic fibers. The dye conforms to the formula

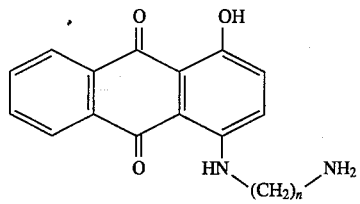

in which n is 2 to 6. The problem of dye uptake at different rates is not mentioned. Only two examples of hair dyeing are described. One example uses only a one dye composition and the other uses two dyes with similar side chains.

British patent 1,159,557 is related to U.S. Pat. No. 4,226,784. Patentees disclose in the '557 patent a composition suitable for dyeing keratinic fibers, particularly human hair. The composition comprises a solution of at least one compound of the formula A—NR—(CH$_2$)$_n$—NHR' in which each of R and R' is independently hydrogen, lower alkyl or lower hydroxy alkyl; n is 2 to 6; and A is either an anthraquinone radical of the formula

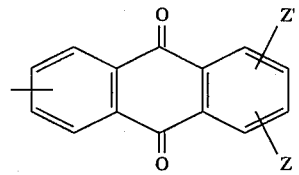

in which case R represents a hydrogen atom, and Z' is hydrogen or —NHR$_1$ wherein R$_1$ is hydrogen or lower alkyl; and Z is hydrogen or —NRR" wherein R is as previously defined and R" is hydrogen, lower alkyl or —(CH$_2$)$_n$—NHR' in which R' and n are as previously defined, the chain NR(CH$_2$)$_n$—NHR' occupying on the anthraquinone nucleus either the 1- position, in which case the radical Z' is a hydrogen atom and the radical Z, unless it is hydrogen, may occupy only the 4-, 5- or 8- position; or the NR(CH$_2$)$_n$—NHR' chain occupies on the anthraquinone nucleus the 2-position, in which case the radical R' and the radicals Z and Z' are all hydrogen; or the NR(CH$_2$)$_n$ NHR' chain occupies the 5- position on the anthraquinone nucleus, in which case the radical R' is hydrogen, and the radical Z' is NHR$_1$ in the 4- position, R$_1$ being as previously defined, and Z is —NHR$_2$ in the 1- position, R$_2$ being hydrogen or lower alkyl. As with the '784 patent, the problem of dye uptake at different rates is not mentioned.

U.S. Pat. No. 3,661,500 discloses hair dyeing compositions containing as the hair coloring agent

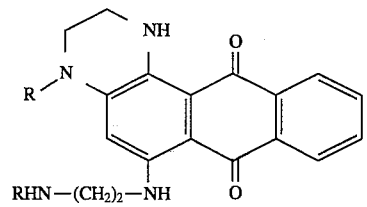

in which R is hydrogen, methyl or ethyl. The examples (e.g. Example #9–12) of this patent vividly illustrate the problems that can occur because of different rates of dye uptake. In these examples, the dyes, their concentrations and the hair are all the same but the above positively charged dye was mixed with typical semipermanent dyes (2-nitro-p-phenylenediamine and 4-nitro-m-phenylenediamine). The only differences between these examples are minor differences in the thickener of the base. Yet, four different colors were obtained: (Example #9) dark greyish brown; (Example #10) medium brown; (Example #11) dark grey; (Example #12) dark ash brown. The dyeing times were not cited and it may be that there were differences and these may account for the color changes.

In French patent of addition 1,422,016, compounds of the formula

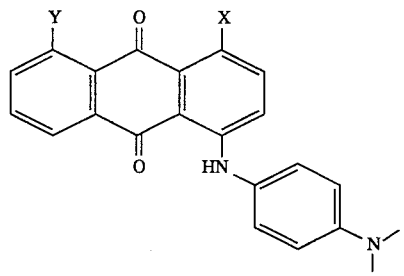

where one of X or Y is H and the other is —HN—p—C$_6$H$_4$—N(CH$_3$)$_2$ or an aminoalkylene-N-morpholino are treated with dimethyl sulfate to give bis-quaternary ammonium salts which dye hair violet red to green shades. Bis-quaternary ammonium salts having the following structures are disclosed:

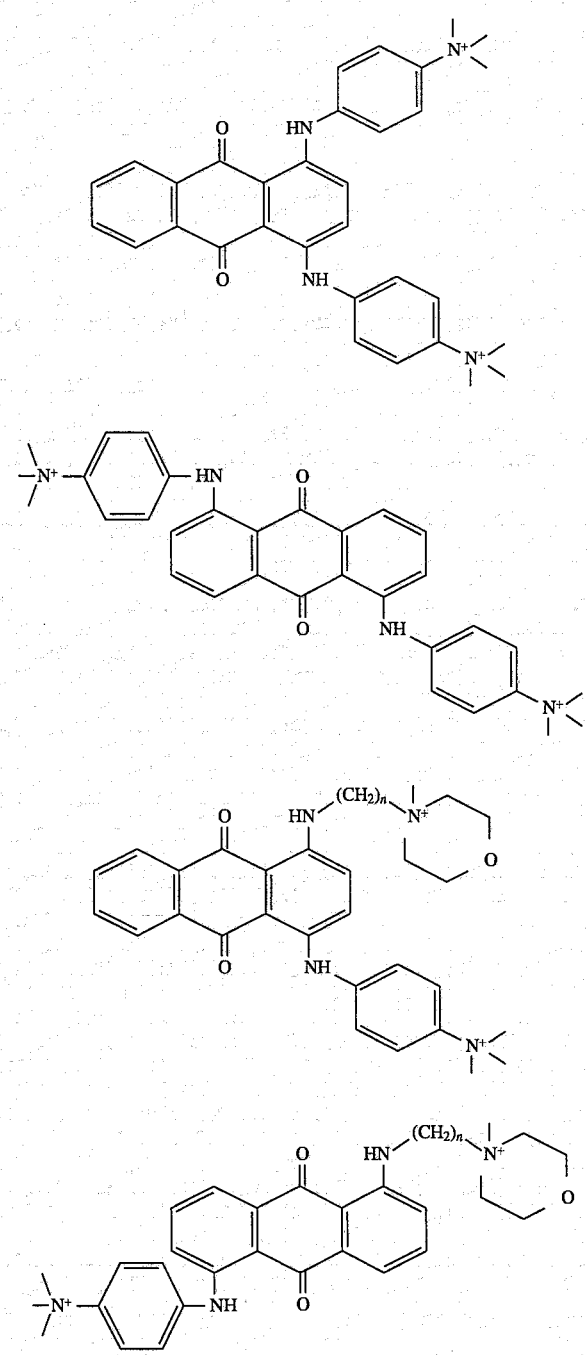

There is no indication that the rate of dye uptake was appreciated and each example uses only one dye.

U.S. Pat. No. 5,314,505 discloses aminoanthraquinone hair dyes having a quaternary center with a long aliphatic chain. Such dyes conform to the general formula $Q—NR_6(CH_2)_nN^+R_1R_2R_3X^-$ wherein Q can be

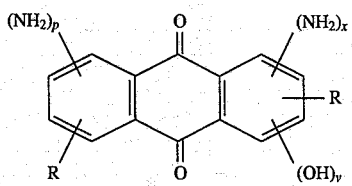

wherein R is hydrogen, $C_{1-6}$ alkyl, $C_{1-6}$ hydroxyalkyl, $C_{1-6}$ polyhydroxyalkyl, halogen, $C_{1-6}$ alkoxy, halogenated $C_{1-3}$ alkyl, polyhalogenated $C_{1-3}$ alkyl, CN, $CONH_2$, $SO_3H$ or COOH; R is $C_{1-6}$ alkyl, $C_{1-6}$ hydroxyalkyl or $C_{1-6}$ polyhydroxyalkyl; $R_2$ is $C_{1-6}$ alkyl, $C_{1-6}$ hydroxyalkyl or $C_{1-6}$ polyhydroxyalkyl; $R_3$ is $C_{8-22}$ aliphatic chain; $R_4$ and $R_5$ are independently, hydrogen, $C_{1-6}$ alkyl, $C_{1-6}$ hydroxyalkyl or $C_{1-6}$ polyhydroxyalkyl or together with N, a 5 or 6 member heterocyclic ring; $R_6$ is hydrogen, $C_{1-6}$ alkyl, $C_{1-6}$ hydroxyalkyl or $C_{1-6}$ polyhydroxyalkyl; n is 2 to 12; and p, q, x and y are independently 0, 1 or 2. Again, each example uses only one dye and the problem of different rates of dye uptake is unappreciated by patentees.

As is evident from U.S. Pat. Nos. 5,314,505, 5,298,029, 5,256,823, 5,198,584, 5,169,403, 5,139,532 and 5,135,543 there is continued interest in hairdyes with side chains containing quaternary ammonium salts. As noted above, the prior art does appreciate that incorporating in a single formulation dyes having different rates of dye uptake can present a serious problem to product performance. Considering the paucity of information on the rate of dye uptake, it is not hard to understand that there has been no appreciation prior to the present disclosure that minor changes in the quaternary ammonium side chain of a basic dye can significantly effect the rate of dye uptake. The teaching of the Robbins et al paper discussed earlier indicates that it would not.

The present invention provides novel anthraquinones having a quaternary ammonium side chain. The compounds of the invention are useful as hair dyes and, more particularly, as semipermanent blue hair dyes in formulations containing neutral semipermanent dyes.

The novel compounds of the instant invention have the structures:

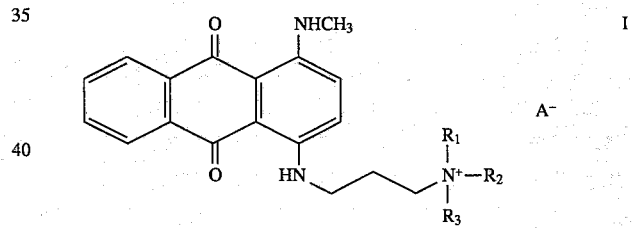

Formula I emcompasses the novel compounds Ia and Ib as follows:

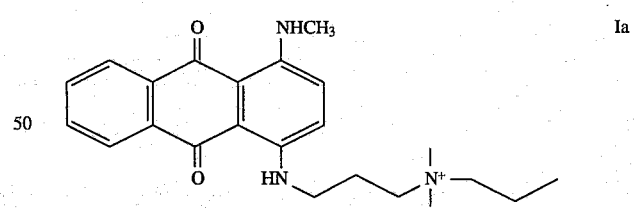

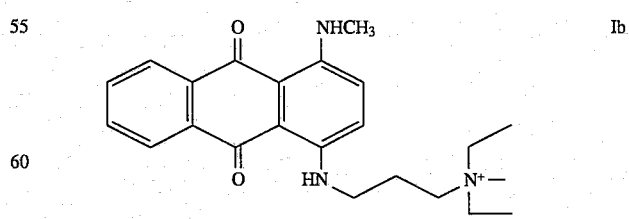

The anthraquinones of formula I surprisingly dye hair at a rate such that they can be used in formulations containing typical neutral semipermanent dyes.

It should be noted that as used throughout this specification and claims $A^-$ connotes a cosmetically acceptable anion such as a halide e.g. iodide, chloride, bromide, fluoride, an alkylsulfate e.g. methylsulfate, or an alkylcarboxylate e.g. acetate. Iodide is the most preferred.

The compounds of Tables 1 and 2 (including compounds I and II of the present invention) were synthesized by the following general procedure.

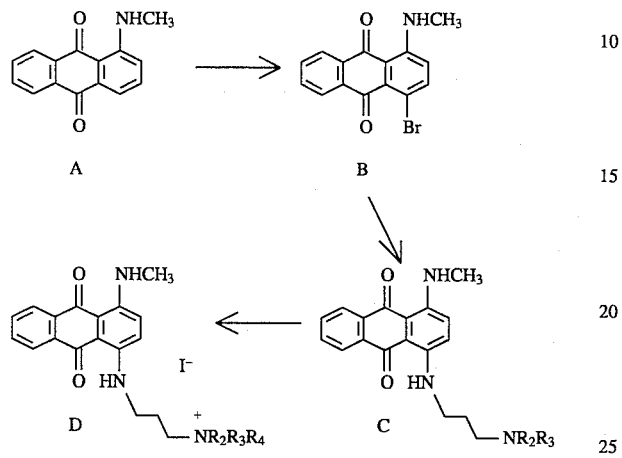

1-Bromo-1-methylaminoanthraquinone was prepared by bromination of 1-methylaminoanthraquinone with N-bromosuccinimide in DMF at 4° C. An Ullman type substitution on 1-bromo-1-methylamino-anthraquinone was performed with 20 wt % copper powder and 3-dimethylaminopropylamine (or 3-diethylaminopropylamine) in DMSO at 80° C. to produce compound C (wherein $R_1$ and $R_2$ are methyl when 3-dimethylaminopropylamine is employed or $R_1$ and $R_2$ are ethyl when 3-diethylaminopropylamino is employed). The reaction mixture was hot filtered through Celite to remove the insoluble copper. Quaternization of compound C (wherein $R_1$ and $R_2$ are methyl or $R_1$ and $R_2$ are ethyl) was performed in DMF with various iodoalkanes (see Tables I and II) to afford compound D.

EXAMPLE 1

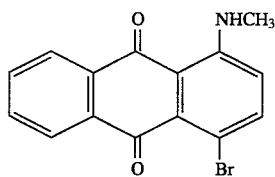

The resultant compound so produced had a melting point of 192.5°–193.6° C. and the following $H^1$NMR:

(300 MHz, DMSO-d6) δ 2.99 (d, 3H, J=4.8 Hz), 7.11 (d, 1H, J=9 Hz), 7.79–7.89 (m, 3H), 8.06–8.13 (m, 2H), 9.87 (bs, 1H, exchange with $D_2O$).

EXAMPLE 2

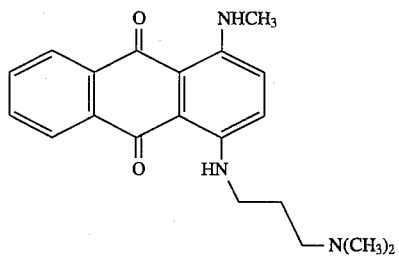

The resultant compound so produced had a melting point of 111.0°–112.5° C. and the following $H^1$NMR:

(300 MHz, DMSO-d6) δ 1.76 (m, 2H), 2.13 (s, 6H), 2.31 (m, 2H), 3.05 (t, 3H, J=5.0 Hz), 3.44 (t, 2H, J=2.4 Hz), 7.41–7.53 (m, 2H), 7.74–7.78 (m, 2H), 8.20–8.23 (m, 2H), 10.65 (bs, 1H, exchange with $D_2O$), 10.84 (bs, 1H, exchange with $D_2O$).

EXAMPLE 3

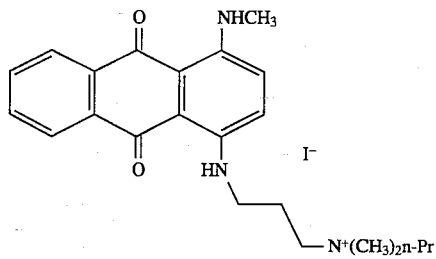

The resultant compound so produced had a melting point of 227.0°–228.3° C. and the following $H^1$NMR:

(300 MHz, DMSO-d6) δ 0.87 (t, 3H, J=7 Hz), 1.63–1.71 (m, 2H), 2.06–2.09 (m, 2H), 3.01 (s, 6H), 3.07 (d, 3H, J=5 Hz), 3.23 (m, 2H), 3.36 (m, 2H) 3.53 (m, 2H), 7.44–7.56 (m, 2H), 7.77–7.80 (m, 2H), 8.21–8.24 (m, 2H), 10.60 (m, 1H, exchange with $D_2O$), 10.78 (m, 1H exchange with $D_2O$).

EXAMPLE 4

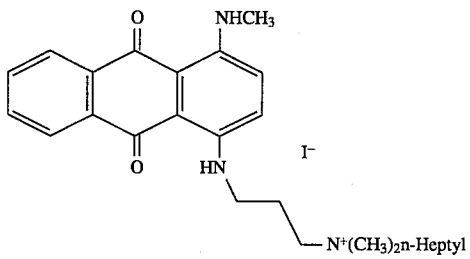

The resultant compound so produced had a melting point of 160.2°–161.7° C. and the following $H^1$NMR:

(300 MHz, DMSO-d6) δ 0.80 (s, 3H), 1.19 (s, 8H), 1.59–1.60 (s, 2H), 2.04–2.05 (s, 2H), 3.01(s, 6H), 3.07–3.08 (d, 4H), 3.24–3.26 (m, 3H), 3.52–3.53 (m, 2H), 7.44–7.56 (m, 2H), 7.78–7.80 (m, 2H), 8.22–8.23 (m, 2H), 10.61 (d, 1H, exchange with $D_2O$), 10.79 (s, 1H, exchange with $D_2O$).

EXAMPLE 5

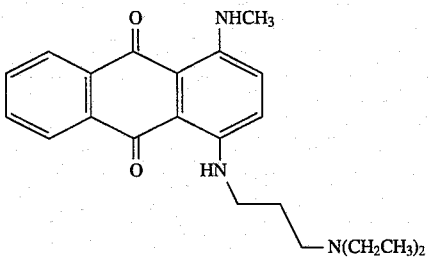

The resultant compound so produced had a melting point of 70.0°–71.7° C. and the following $H^1$NMR:

(300 MHz, DMSO-d6) δ 0.91–0.96 (t, 6H), 1.68–1.78 (m, 2H), 2.41–2.48 (m, 6H), 3.05–3.07 (d, 3H), 3.42–3.48 (m, 2H), 7.42–7.52 (m, 2H), 7.75–7.78 (m, 2H), 8.20–8.23 (m, 2H), 10.64–10.66 (d, 1H, exchange with $D_2O$), 10.83–10.87 (t, 1H, exchange with $D_2O$).

EXAMPLE 6

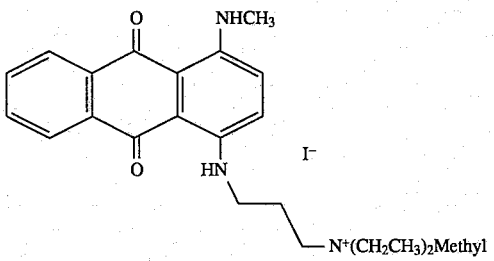

The resultant compound so produced had a melting point of 176.0°–177.7° C. and the following $H^1$NMR:

(300 MHz, DMSO-d6) δ 1.20 (t, 6H, J=7 Hz), 2.03 (m, 2H), 2.92 (s, 3H), 3.07 (d, 3H, J=5 Hz), 3.31 (m, 6H), 3.54 (m, 2H), 7.45–7.57 (m, 2H), 7.77–7.80 (m, 2H), 8.21–8.23 (m, 2H), 10.60 (bs, 1H, exchange with $D_2O$), 10.78 (bs, 1H, exchange with $D_2O$).

EXAMPLE 7

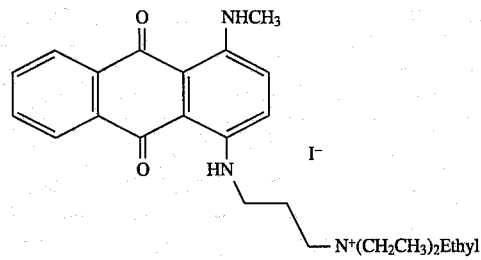

The resultant compound so produced had a melting point of 180.0°–183.8° C. and the following $H^1$NMR:

(300 MHz, DMSO-d6) δ 1.14–1.18 (t, 8H), 1.96–2.01 (m, 2H), 3.07–3.09 (d, 3H), 3.21–3.28 (m, 9H), 3.53–3.55 (m, 2H), 7.45–7.57 (m, 2H), 7.77–7.81 (m, 2H), 8.21–8.23 (m, 2H), 10.61–10.62 (d, 1H, exchange with $D_2O$), 10.78–10.82 (t, 1H, exchange with $D_2O$).

All compounds (except for the heptyl compounds) were purified by recrystallization from isopropyl alcohol and water or methanol. The heptyl compound was used without recrystallization. After recrystallization, they were then dried under vacuum over $P_2O_5$ at 65° C. overnight and analyzed by HPLC. That analysis showed the purity to be at least 90%. Tresses of Piedmont hair weighing 1.25 g were dyed for time specified at room temperature with 10 g of 0.5% solutions of 4-(N,N,N-trialkyl-3'-ammonium-n-propylamino)-1-methylamino-anthraquinone iodide in a commercially available hair dye base. It should be noted that as used herein, unless otherwise indicated, percent means percent by weight and is based on the total weight. The dyed tresses were rinsed under tap water for 1–2 minutes and dried. The tristimulus reflectance values of the dyed swatches were determined by means of a Hunterlab LabScan 6000 0°/45° Spectrocolorimeter. Untreated swatches were used as a control. The results are reported in Table 1 which follows.

It should be noted that "L" represents the intensity of the color and "a and b" represent the relative purity of the color with "a" being the relative greenness or redness of the color and "b" being the relative yellowness or blueness of the color. ΔE, shown in Table 2, is the total color difference and is defined by the equation:

$$\Delta E = \sqrt{(\Delta L)^2 + (\Delta a)^2 + (\Delta b)^2}$$

Δ's (e.g. ΔL, Δa, Δb) refer to the change in that parameter for some operation. For example, ΔL for 0→15 minutes is the change in L on dyeing from 0 minutes to 15 minutes. It should be further noted that in Table 1, the Piedmont hair had the following Hunter Reflectance Values prior to being dyed with the test compounds: L=69.4, a=−0.7, b=21.8

From the Hunter reflectance values in Table 1 and the ΔE's in Table 2, it can be seen that almost all of the dye uptake of the trimethyl compound occurs in the first 15 minutes. At 30 minutes, the color of hair dyed with the trimethyl compound stops changing. In comparison (by examining principally ΔE's in Table 2), HC Blue 2 initially does not dye as rapidly but then keeps on dyeing even at 60 minutes. At first glance, it may appear from Table 1 that the trimethyl compound and HC Blue 2 are more similar than the other compounds to HC Blue 2. This is due to the similarity of the L values. However, this is misleading because these anthraquinones are bright blue while HC Blue 2 is actually violet. ΔE is a much better indicator when different colors are involved. The data of Table 2 shows how much more rapid the dye uptake is for the trimethyl compound ($\Delta E_{0 \to 15}$=44.7) in comparison to HC Blue 2 ($\Delta E_{0 \to 15}$=37.2). The other three compounds in Table 2 are much closer to HC Blue 2 in their initial color changes. Between 15 and 30 minutes, the color changes of hair dyed with the trimethyl compound and HC Blue 2 are similar but after 30 minutes hair dyed with the trimethyl compound essentially stops changing color. These qualitative differences (faster initial color change and the color change ending after 30 minutes for the trimethyl compound) between the trimethyl compound and HC Blue 2 demonstrate that the trimethyl compound is unacceptable for use with typical semipermanent dyes.

The triethyl and the heptyl, dimethyl compounds demonstrate other unacceptable attributes. The heptyl compound (and most higher alkyl derivatives) has a very low dye uptake; for example, as shown by Table 1, after 60 minutes of dyeing the Hunter values are only L=50.7, a=−8.8, b=1.4. Obviously, a dye which does not impart much color is of little value. The triethyl compound, according to $\Delta E_{0 \to 15}$, is similar to HC Blue 2 initially but after 15 minutes, its dye uptake is much lower than HC Blue 2. If this compound were used in combination with a neutral

TABLE 1

The Hunter Reflectance Readings (L,a,b) for Piedmont Hair Dyed with 4-(N,N,N-Trialkyl-3'-Ammonium-n-Propylamino)-1-Methylaminoanthraquinones Iodide, I, in a Commercial Hairdye Base
Hunter Reflectance Readings (L,a,b)

| Substitutents on the Quaternary Ammonium Group | Dyeing Time | | |
|---|---|---|---|
| | 15 minutes | 30 minutes | 60 minutes |
| Trimethyl | 39.1, −5.6, −11.3 | 35.9, −5.2, −15.0 | 34.2, −4.7, −15.6 |
| (Basic Blue 22) | 39.4, −5.7, −10.4[1] | 34.7, −4.8, −13.6[1] | 35.7, −5.1, −14.6[1] |
| average | 39.2, −5.6, −10.8[2] | 35.3, −5.0, −14.3[2] | 35.0, −4.9, −15.1[2] |
| Propyl, Dimethyl (Ia) | 44.6, −7.3, −6.8 | 43.4, −6.1, −10.4 | 39.9, −7.0, −11.6 |
|  | 43.3, −7.6, −7.3[1] | 42.5, −7.4, −9.3[1] | 39.8, −6.8, −12.1[1] |
| average | 44.0, −7.4, −7.0[2] | 43.0, −6.8, −9.8[2] | 39.8, −6.9, −11.8[2] |
| Heptyl, Dimethyl | 55.7, −8.0, 6.3 |  | 50.7, −8.8, 1.4 |
| Diethyl, Methyl (Ib) | 43.0, −7.3, −6.5 | 42.3, −6.6, −9.5 | 40.2, −6.8, −10.4 |
| Triethyl | 45.1, −7.4, −5.9 | 43.8, −7.3, −6.9 | 43.0, −7.4, −9.2 |
| HC Blue 2[3] | 41.1, 4.7, −1.7 | 36.0, 5.9, −4.7 | 34.2, 6.5, −6.8 |

[1]Entire dyeing experiment repeated.
[2]The average of these two experiments will be used in subsequent calculations.
[3]A direct dye (i.e. semipermanent dye) evaluated for comparative purposes

TABLE 2

The Total Color Change (ΔE) of Piedmont Hair Dyed with 4-(N,N,N-Trialkyl-3'-Ammonium-n-Propylamino)-1-Methyl-aminoanthraquinones Iodide, I, for Different Lengths of Time

| Substituents on the Quaternary Ammonium Group | ΔE | | | |
|---|---|---|---|---|
| | 0→15 min. | 15→30 min. | 30→60 min. | 15→60 min. |
| Trimethyl (Basic Blue 22) | 44.7 | 5.3 | 0.9 | 6.0 |
| Propyl, Dimethyl (Ia) | 39.0 | 3.0 | 3.8 | 6.4 |
| Heptyl, Dimethyl | 21.9 |  |  | 7.0 |
| Diethyl, Methyl (Ib) | 39.3 | 3.2 | 2.3 | 4.8 |
| Triethyl | 37.4 | 1.6 | 2.4 | 3.9 |
| HC Blue 2[1] | 37.2 | 6.0 | 2.8 | 8.8 |

[1]A direct dye (i.e. semipermanent dye) evaluated for comparative purposes semipermanent dye, the color (i.e. shade and intensity as opposed to only the intensity) would vary after 15 minutes. Thus, this compound is unacceptable.

While the propyl, dimethyl (Ia) and the diethyl, methyl (Ib) are not perfect matches for HC Blue 2, they are the closest fit and give the overall best combination of properties. During the first 15 minutes of dyeing, the rate of color change on hair with both of these compounds is just slightly faster than that of HC Blue 2. Thereafter, their rate of color change is slightly less than that of HC Blue 2, as evident by their ΔE's in Table 2. It is surprising and unexpected that: (1) hair dyed with the trimethyl compound would stop changing color after a particular period of time; (2) the rate of color change on hair with the trimethyl could be modified by minor changes in the alkyl groups on the quaternary ammonium center, and; (3) this minor change in the alkyl groups modifies the rate of color change so that the so modified compound can be used with neutral semipermanent dyes.

The present invention includes the novel compounds of Formulae Ia and Ib, compositions containing a tinctorially effective amount of either compound with neutral semipermanent dyes in a cosmetically acceptable vehicle and a method for dyeing a keratin fiber by contacting such fiber with either compound Ia or Ib.

Dye compositions employing the anthraquinone dyes of the present invention may be formulated as a solution, a liquid shampoo (which can be a solution or an emulsion), a cream, a gel, a powder, or an aerosol.

Examples of the semipermanent dyes with which these compounds can be used can be found in any of the numerous reviews on hair dyes such as the one by J. F. Corbett in the Review of the Progress of Coloration, Volume 15, pages 52–65, (1985). Examples of these dyes are: N-(2'-Hydroxyethyl)-o-nitroaniline, 4-Nitro-o-phenylenediamine, N1-(2-Hydroxyethyl)-4-nitro-o-phenylenediamine, N1-Tris(hydroxymethyl)methyl-4-nitro-o-phenylenediamine, 2-Amino-3-nitrophenol, 2-Amino-4-nitrophenol, 4-Amino-2-nitrophenol, 2-Amino-5-nitrophenol, O,N-Bis(2'-hydroxyethyl)-2-amino- 5-nitrophenol, N-(2'-Hydroxyethyl)-2-amino-5-nitroanisole, 4-Amino-3-nitrophenol, N-(2'-Hydroxyethyl)-4-amino-3-nitrophenol, N-(2'-Hydroxyethyl)-4-amino-3-nitroanisole, 1-(3-Methylamino-4-nitrophenoxy)propane- 2,3-diol, 3-Methylamino-4-nitrophenoxyethanol, 2-Nitro-p-phenylenediamine, N1-(2'-Hydroxyethyl)-2-nitro-p-phenylenediamine, N4-(2'-Hydroxyethyl)-2-nitro-p-phenylenediamine, N1-Methyl-2-nitro-p-phenylenediamine, N1,N4,N4-Tris-(2'-hydroxyethyl)-2-nitro-p-phenylenediamine, N4-(2'-Hydroxyethyl)-N 1,N4-dimethyl-2-nitro-p-phenylenediamine, N4-(2',3'-Di-hydroxypropyl)-N 1,N4-dimethyl-2-nitro-p-phenylenediamine, 4-Nitro-m-phenylenediamine, Picramic Acid, N-Methyl-isopicramic acid, 4-Amino-2-nitrodiphenylamine, 4-Hydroxy-2'-nitrodiphenylamine, 4-(p-Aminophenylazo)-N,N-bis(2'-hydroxyethyl)aniline, 1,4,5,8-Tetraaminoanthraquinone, 1,4-Diaminoanthraquinone, 1-Amino-4-methylaminoanthraquinone, 1-(2'-Hydroxyethylamino)-4-methylaminoanthraquinone, 2,4-Diamino-2'-hydroxy-5'-nitroazobenzene- 5-sulphonic acid (Na salt). These dyes may be incorporated with the anthraquinones of the present invention provided such agents do not interfere with the dyeing ability of these dyes or react with them.

Materials typically included in hair dye compositions and/or developers include for example, organic solvents and solubilizing agents, surface active agents, thickening agents, buffers, chelating agents, perfumes, sunscreens, conditioners, dyeing assistants or penetrating agents, preservatives, emulsifiers and fragrances. A particular material may perform several functions. For example, a surfactant may also act as a thickener. The dye compounds of formulas I are cationic. The dye uptake of cationic dyes is inhibited by an excess certain anionic materials with which the cationic dyes would complex, precipitate or similarly react. Consequently, care should be exercised in formulating with such materials.

It is often advantageous to include in the dye compositions of the present invention an organic solvent or solvent system which helps solubilize the dyes and adjuvants contained in the compositions. A number of organic solvents are known for such purpose. These include: alcohols, particularly alkyl alcohols of 1–6 carbons, especially ethanol and propanol; glycols of up to about 10 carbons, preferably less than 6 carbons, especially propylene glycol and butylene glycol; glycol ethers of up to about 10 carbons, especially diethyleneglycol monobutyl ether; carbitols; and benzyl alcohol. When present, the solvents will constitute from about 1% to about 60%, preferably from about 10 to about 30%, by weight of the dyeing composition.

Typical surfactant types useful in the compositions of the invention include: alkyl sulfates, alkyl ether sulfates, amide ether sulfates, soaps, alkyl ether carboxylates, acylsarcosinates, protein/fatty acid condensates, sulfosuccinic acid esters, alkane sulfonates, alkylbenzene sulfonates, a-olefin sulfonates, acylisethionates, acyltaurines, ethoxylates, sorbitan esters, alkanolamides, amine oxides, quaternary ammonium salts, alkyl betaines, amidopropyl betaines, sulfobetaines, glycinates/aminopropionates and carboxyglycinates/aminodipropionates. A combination of different surfactants can be used to impart particular viscosity and foaming properties.

Illustrative of specific surfactants that may be employed are: lauryl sulfate; polyoxyethylene lauryl ester; myristyl sulfate; glyceryl monostearate; sodium salt of palmitic acid, methyl taurine; cetyl pyridinium chloride; lauryl sulfonate; myristyl sulfonate; lauric diethanolamide; polyoxyethylene stearate; stearyl dimethyl benzyl ammonium chloride: dodecyl benzene sodium sulfonate; nonyl naphthalene sodium sulfonate; dioctyl sodium sulfosuccinate; sodium N-methyl-N-oleyl taurate; oleic acid ester of sodium isethionate; sodium dodecyl sulfate, and the like. The quantity of water soluble surface active agent employed can vary widely up to about 15%. Preferably, the surface active agent is employed in an amount of from about 0.10% to about 10%, based on the weight of the composition. Note however that when an anionic surfactant is employed the amount must be restricted so as to avoid possible incompatibility with the dye compounds of the present invention.

The thickening agent, when employed, may be one or a mixture of those commonly used in hair dyeing compositions or in hair developers. Such thickening agents include: sodium alginate; gum arabic; cellulose derivatives, such as methylcellulose or the sodium salt of carboxymethylcellulose; acrylic polymers, such as polyacrylic acid sodium salt; and inorganic thickeners, e.g., bentonite and fumed silica. Electrolytes, alkanolamides, cellulose ethers and highly ethoxylated compounds (such as ethers, esters and diesters) may also be used to thicken the composition. The quantity of thickening agent can vary over a wide range. Typically the thickening agent(s) is employed in an amount of up to about 20%, more preferably, from about 0.1% to 5%, based on the weight of the composition.

The pH of the dye composition can vary from about 2.5 to about 11. Any compatible water-dispersible or water soluble alkalizing agent can be incorporated in the composition in an amount suitable to give the desired pH. Typically, the amount of alkalizing agent employed is less than about 10%, preferably, from about 0.1 % to about 5%, based on the weight of the composition.

Compatible alkalizing agents are those which under the conditions of use do not interact chemically with the dye(s) employed, that do not precipitate the dye(s), and are non-toxic and non-injurious to the scalp. Preferred alkalizing agents include: mono-, di- and trialkanolamines, such as triethanolamine and 2-amino-2-methyl-1,3-propanediol; alkyl amines, such as monoethylamine, diethylamine and dipropylamine; and heterocyclic amines, such as morpholine, piperidine, 2-pipecoline and piperazine.

Any inorganic or organic acid or acid salt, that is compatible with the dye composition and does not introduce toxicity under its conditions of use, can also be employed to adjust the pH of the dye composition. Illustrative of such acids and acid salts are sulfuric acid, formic acid, acetic acid, lactic acid, citric acid, tartaric acid, ammonium sulfate, sodium dihydrogen phosphate, and potassium bisulfate.

Common chelating agents that can be employed in the compositions of the invention include the salts of ethylenediaminetetraacetic acid (EDTA), nitrilotriacetic acid, phosphates, pyrophosphates and zeolites.

Conditioners that can be incorporated in the present compositions include: encapsulated silicones; silicones, such as amino functional and carboxy silicones; volatile silicones; combinations of a cationic polymer, a decomposition derivative of keratin and a salt; quaternary ammonium compounds such as cocos—$(C_{12-18})$-alkyl poly (6) oxyethyl di-(2-lauroyloxyethyl)-methyl ammonium chloride; combinations of a plant extract and a polypeptide; a dimethyl diallyl ammonium chloride (DMDAAC)/acrylic acid type polymer; and a dialkyl quaternary ammonium compound where the alkyl groups are $C_{12}$–$C_{16}$. Other well known conditioners, such as lanolin, glycerol, oleyl alcohol, cetyl alcohol, mineral oil and petrolatum, can also be incorporated.

It is a common practice to add solvents or swelling agents to enhance the penetration of hair dyes. Materials useful for swelling hair include acetic acid, formic acid, formamide, urea, ethyl amine and certain alkali halides (potassium iodide, sodium bromide, lithium bromide and lithium chloride, but not sodium chloride). N-Alkyl pyrrolidones and epoxy pyrrolidone may be employed to potentially increase the penetration of dye into hair. Imidazolines such as disclosed in U.S. Pat. No. 5,030,629 may be employed in the compositions to enhance the penetration of hair dyes.

Emulsifiers may be used when the final form of the hair dye is an emulsion. Many emulsifiers are by their nature also surfactants. There are five general categories: anionic, cationic, nonionic, fatty acid esters and sorbitan fatty acid esters. Examples include: mono-, dialkyl and trialkyl ether phosphates, long-chain fatty acids with hydrophilic compounds such as glycerin, polyglycerin or sorbitol and long chain alkyl primary and secondary amines, quaternary ammonium and quaternary pyridinium compounds.

Materials which may render the product aesthetically more appealing, such as fragrances, proteins hydrolysates, vitamins and plant extracts, may be added. Examples include chamomile, aloe vera, ginseng, and pro-vitamin B.

What is claimed is:

1. A method for dyeing a hair fiber on a living human head comprising contacting said fiber with a tinctorially effective amount of an anthraquinone compound of formula I

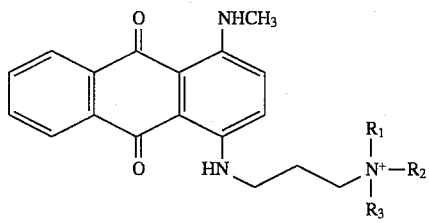

wherein $R_1$ and $R_2$ are methyl and $R_3$ is propyl, or $R_1$ and $R_2$ are ethyl and $R_3$ is methyl, and $A^-$ is a cosmetically acceptable anion, in a cosmetically acceptable vehicle; said contacting being for a time sufficient to dye said fiber.

2. The method, as claimed in claim 1, wherein in the anthraquinone compound of formula I, $R_1$ and $R_2$ are methyl and $R_3$ is propyl.

3. The method, as claimed in claim 1, wherein in the anthraquinone compound of formula I, $R_1$ and $R_2$ are ethyl and $R_3$ is methyl.

4. The method, as claimed in claim 1, wherein the anion is selected from the group consisting of iodide, chloride, bromide, fluoride, methylsulfate, and acetate.

5. The method, as claimed in claim 1, wherein said fiber is simultaneously contacted with at least one direct dye.

* * * * *